United States Patent [19]

Evens et al.

[11] Patent Number: 5,140,169
[45] Date of Patent: Aug. 18, 1992

[54] LONG PATH FLOW CELL RESISTANT TO CORROSIVE ENVIRONMENTS FOR FIBER OPTIC SPECTROSCOPY

[75] Inventors: F. Monte Evens; Craig T. Barker, both of Ponca City; Charles R. Ray, Blackwell, all of Okla.

[73] Assignee: Conoco Inc., Ponca City, Okla.

[21] Appl. No.: 693,115

[22] Filed: Apr. 25, 1991

[51] Int. Cl.$^5$ .............................................. H01J 5/16
[52] U.S. Cl. ............................... 250/576; 250/227.11; 250/227.25; 356/246
[58] Field of Search ................... 250/576, 564, 227.21, 250/227.23, 227.25, 343, 432 R, 227.11; 356/246, 410, 440, 338

[56] References Cited

U.S. PATENT DOCUMENTS

| | | |
|---|---|---|
| 3,513,319 | 5/1970 | Broerman ........................ 250/227.25 |
| 4,008,397 | 2/1977 | Zdrodowski . |
| 4,260,257 | 4/1981 | Neeley et al. . |
| 4,319,138 | 3/1982 | Sweet ................................ 250/576 |
| 4,540,280 | 9/1985 | Anderson . |
| 4,588,893 | 5/1986 | Vidrine et al. . |
| 4,668,091 | 5/1987 | Lagesson et al. .................... 356/246 |

Primary Examiner—David C. Nelms
Assistant Examiner—K. Shami

[57] ABSTRACT

A flow cell for use in highly corrosive environments is constructed from an extended metal body containing a smooth longitudinal circular center bore of uniform cross-section. The metal body contains a circular opening at each end extending perpendicularly into the center bore, adapted to receive a sample into the center bore and discharge the sample from the center bore. A circular connector having a larger diameter than the center bore is contained in each of the opposing ends of the center bore, abutting the solid body to form a right angle shoulder between the inside of the connector and the solid body. Opposing fiber optic probes each with an external sapphire window which is sealed into a metal tube contained in each probe with melted glass and an optional plastic seal over the melted glass are contained in the circular connectors, each said window extending into the center bore a sufficient distance so that the face of said window is in vertical alignment with the nearest internal surface of the circular opening into the center bore. An o-ring gasket is positioned between the right angle shoulder and metal tube end to form a tight cover over the glass seal (and plastic seal) when the probes are assembled in the flow cell, thereby protecting the glass seal (and plastic seal) from the corrosive environment.

28 Claims, 3 Drawing Sheets

LONG PATH FLOW CELL RESISTANT TO CORROSIVE ENVIRONMENTS FOR FIBER OPTIC SPECTROSCOPY

BACKGROUND OF THE INVENTION

In spectrophotometry, radiation from a source passes through a sample cell to a photodetector which measures the amount of radiation absorbed by the sample fluid in the cell. The output of the detector is a measure of absorbance at a particular wavelength of radiation. The quantitative presence of certain materials in the sample is identified by particular wavelengths characteristically absorbed by the materials. An important use of spectrophotometric detectors is in chromatography wherein the components of a sample are separated in a column and the radiation absorbance of the separated components are then measured by a spectrophotometric detector.

In such detectors, radiation transparent optical windows allow radiation from the source to pass through the cell to the detector. In a common spectrophotometric detector, radiation passes through an entrance window, through the cell in a direction parallel to the flow of sample fluid through the cell, and through an exit window to the detector. Flat windows or plano convex lenses typically have been used. U.S. Pat. No. 4,192,614 to deMey et al. shows a detector assembly with flat windows at the entrance and exit openings in the cell. A lens focuses the radiation in a pattern which converges in the cell.

Another type of commonly used detector has divergent optics with sample fluid flow across a substantially planar radiation field in the cell. Such crossflow cells are typified by the Milton Roy LDC microcell used in conjunction with the LDC Model 1204D spectoMonitor detector. Crossflow cells permit close coupling of the cell to the outlet end of a chromatographic column.

Another type of crossflow cell is available from Guided Wave Inc. of California. The Guided Wave cell comprises a standard one quarter inch cross union adapted to receive opposing fiber optic transmission probes. The probes contain an external sapphire window sealed into a one quarter inch metal tube. The metal tube also contains a suitable collimating lens. The tube which can be made from various materials including 316 stainless steel, Monel 400 or Hastelloy C276 alloys is sealed to the sapphire window with a soft glass frit. The glass frit is fused to prevent leaks between the sapphire window and the inner wall of the one quarter inch tube. An additional epoxy seal is used to coat the outer surface of the fused soft glass seal.

While the Guided Wave flow cell can be used in many services, it cannot be used in a hydrogen fluoride atmosphere or in a hydrogen fluoride, hydrogen chloride, chlorine atmosphere or in the presence of a strong caustic or in any other service where the epoxy and glass seal would be attacked by the materials flowing through the cell.

This application is related to co-pending application Ser. No. 07/546,592 filed in the name of the same inventors. Application Ser. No. 07/546,592 discloses a flow cell for use in highly corrosive environments which is constructed from a cross union and contains opposing fiber optic probes each with an external sapphire window which is sealed into a metal tube contained in each probe with melted glass and an optional plastic seal over the melted glass. Each portion of the cross union containing a probe has a right angle shoulder which abuts the end of the tube containing the sapphire window An o-ring gasket is positioned between the right angle shoulder and metal tube to form a tight cover over the glass seal and plastic seal when the probes are assembled in the flow cell, thereby protecting the glass seal and plastic seal from the corrosive environment. It is stated in the application that probes may be installed in such a cross union at any distance up to two or four centimeters apart in a one quarter inch or one half inch cross union respectively.

It is desirable to provide a flow cell having an optical path length substantially greater than the path length of the cross union disolosed in Ser. No. 07/546,592 which can be used in such corrosive environments and in particular, in such environments at elevated temperatures.

THE PRIOR ART

U.S. Pat. No. 4,008,397, to Zdrodowski discloses a fluorometer flow cell wherein the flow cell is constructed entirely of a light transparent polyfluoroethylene tubing. In addition, the flow cell contains a light source means, excitation filter means, cell holder means and photo detection means.

U.S. Pat. No. 4,260,257, to Neeley et al. relates to a flow cell oonstructed by assembling together tubular components which are heated to form an integral flow cell member. The flow cell has a tubular body member, a debubbler unit and a tubular fluid outlet tower. The body member is made from quartz material and has an open ended bore therethrough which connects to a colorimeter. A pair of light transmitting quartz rods are positioned in the respective open ends of the bore to close them.

U.S. Pat. No. 4,540,280, to Anderson et al. relates to a fiber optic thin-layer cell for use in spectrophotometric analysis of liquid or gaseous materials and a method of use, which consists of utilizing fiber optics in conjunction with low-volume, thin-layer cells.

U.S. Pat. No. 4,588,893, to Vidrine et al. discloses a light-pipe flow cell suitable for use in analyzing high pressure fluids. The flow cell has a main support body with a gold light-pipe element mounted therein, two light transmissive window elements diametrically opposed to each other and a resilient sealing means mounted between each window element and the main support body. The flow cell is connected to an infrared spectrometer.

THE INVENTION

A flow cell suitable for use in a corrosive environment comprising: (1) an extended metal body containing a smooth longitudinal circular center bore of uniform cross-section, (2) a circular opening at each end of the cell body extending perpendicularly into the center bore, adapted to receive a sample entry line at one end of the center bore and a sample discharge line from the other end of the center bore, (3) a circular connector in each of the opposing ends of the cell body communicating axially with the center bore and abutting the cell body, said circular connector having an inside diameter greater than the inside diameter of the center bore, whereby a right angle shoulder is formed between the inside of the circular connector and the abutting cell body surrounding the center bore, (4) a fiber optic probe positioned in each circular connector, each probe having a light-transmitting, transparent window extending from a tube contained in each probe said tube abutting said right angle shoulder, (5) an opening between each tube and light-transmitting window said opening being sealed with a sealing material which is attacked by a corrosive environment, and (6) a corrosive resistant o-ring gasket positioned compressively between the end of each tube and said right angle shoulder thereby protecting the sealing material from the corrosive environment.

In one aspect of the invention, the light-transmitting, transparent window of each fiber optic probe extends into the center bore a sufficient distance so that the face of said window is in vertical alignment with the nearest internal surface of the circular opening into the center bore.

DETAILED DESCRIPTION OF THE INVENTION

Figure 1:
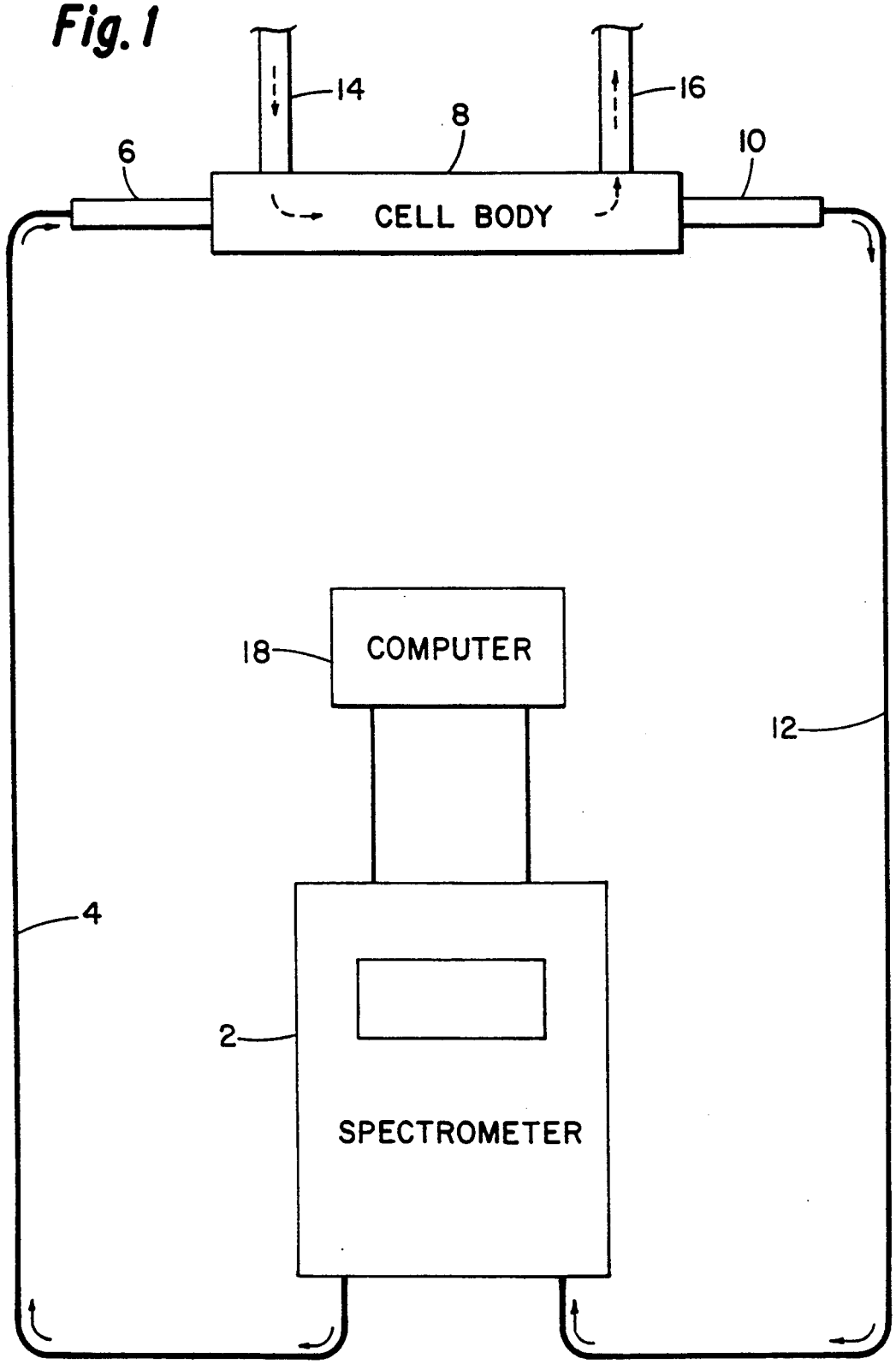
FIG. 1 is a schematic illustration fiber optic flow cell coupled to a spectrometer and a computer.

The invention is best described by reference to the drawings. FIG. 1 is a schematic diagram which illustrates the use of an extended metal cell body containing fiber optic probes in association with a spectrometer and a computer. Spectrometer 2 contains an appropriate radiation source which may be a tungsten-halogen lamp, deuterium arc, laser, or other suitable source. Source light is launched by focusing the radiation source on to a large diameter, single fiber cable 4 which then ducts the light to fiber optic probe 6 which is inserted in cell body 8. A sample, of which the absorbance is to be measured, is introduced to cell body 8 through line 14 and exits through line 16. The source light passes through probe 6 and the sample stream flowing through cell body 8, is received by a similar probe 10 and is returned to spectrometer 2 through optical fiber cable 12.

The sample passing through cell body 8 absorbs part of the light at a specific wavelength which is contained in the source light. When the source light returns to the spectrometer, the percentage of this wavelength absorbed is determined. Through the use of a suitable curve, relating concentration to wavelength absorbance for the sample, the concentration of the material being measured in the sample stream is determined. By use of computer 18 with an appropriate computer program, the output of the spectrometer is processed and periodically provides the desired concentration printout or reading. In this manner, changes in concentration of the flowing sample may be determined with desired frequency and operating conditions or parameters may be adjusted in response to such changes in concentration.

Figure 2:
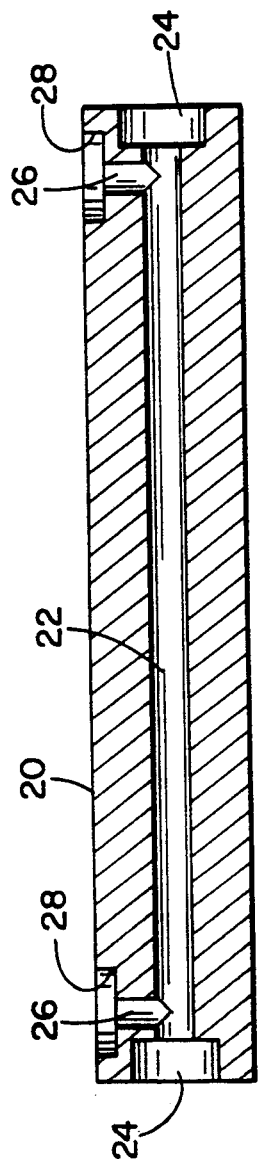
FIG. 2 is an illustration in cross-section of an extended metal cell body with a longitudinal center bore adapted to receive fiber optic probes.

FIG. 2 illustrates in cross-section an extended metal cell containing a smooth longitudinal circular center bore 22 of uniform cross-section. A circular opening 24 in longitudinal alignment with center bore 22 is provided in each end of the cell body. Openings 24 are sized to receive male pipe weld connectors. Circular openings 26 are provided at each end of the cell body extending perpendicularly into center bore 22. Usually openings 26 will have substantially the same cross-section as center bore 22. Larger openings 28 are provided in cell body 20 in axial alignment with openings 26. The larger openings 28 are also sized to receive male pipe weld connectors.

Figure 3:
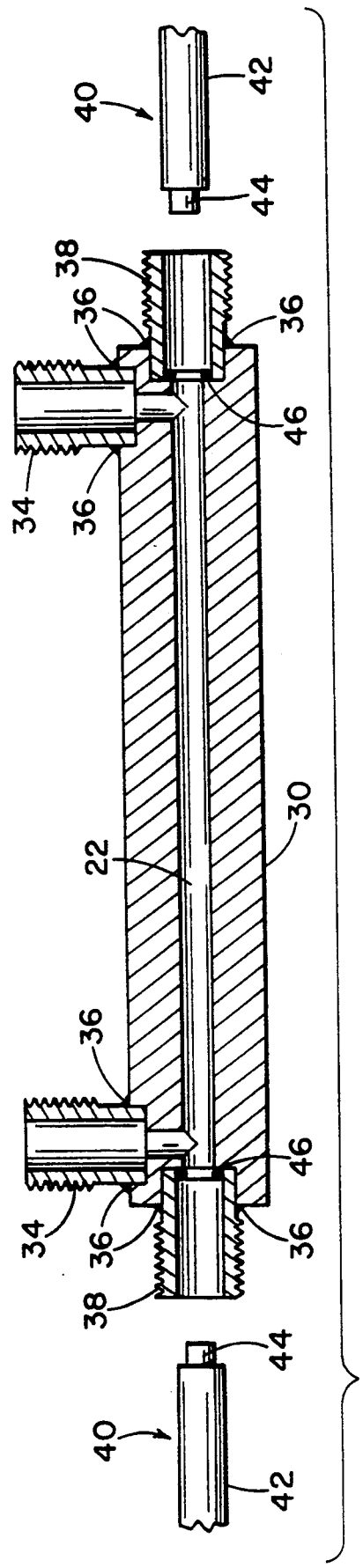
FIG. 3 is a more detailed schematic illustration in cross-section of the metal cell body, including non-assembled fiber optic probes.

FIG. 3 illustrates an extended metal cell body 30 which is the same as cell body 20. In this figure, male pipe weld connectors 34 and 38 have been installed in the four openings provided in the metal cell body for this purpose. To provide a high pressure fit of these connectors, each connector is welded to cell body 30 at 36. Suitable attachments may be made to connectors 34 to provide for entry of sample into the cell body and exit of sample from the cell body.

The opposing connectors 38 are sized to receive fiber optic probes, both of which are designated in part by 40. The end portion of each fiber optic probe 40 which is inserted in a connector 38 comprises a tube 42 in to which there is inserted a transparent, light transmitting optical window 44 made of sapphire or other suitable material. The space between window 44 and tube 42 is sealed with a suitable sealing material such as melted glass (not shown). As used herein the term "melted glass" means glass which has been fused or melted and allowed to harden to form a suitable seal. An additional sealing material (not shown) e.g. a plastic material such as epoxy may be applied over the glass sealing. For ease of installation, window 44 is slightly tapered in the direction in which it is placed in tube 42.

The inside diameter of each connector 38 is slightly greater than the diameter of center bore 22 so that a right angle shoulder is formed between the inside surface of each connector 38 and the abutting cell body 30. An o-ring gasket 46 is placed in each connector 38 and is positioned adjacent the right angle shoulder. When the fiber optic probes 40 are inserted in connectors 38, the right shoulder formed by the connectors abuts the end portion of tubing 42 which extends outwardly from window 44 thereby compressing the o-ring gasket around the seal between tubing 42 and window 44. The position of the shoulders including the compressed O-rings sets the optical path length of the probe.

The light-transmitting, transparent window 44 in each probe preferably is extended into center bore 22 a sufficient distance so that the face of the window is in vertical alignment with the nearest internal surface of the circular perpendicular opening into the center bore. This position of the window is obtained by the proper location of the shoulder formed by connector 38. By locating the window in this manner, the dead volume zone for sample flow in and out of the cell is reduced to a minimum.

The center bore 22 of the flow cell is sufficiently large to accept the light transmitting window while not producing excessive void volume for sample flow. The center bore should be as smooth as possible so as to prevent any turbulence of liquid flow and to minimize scattering of transmitted light throughout the optical path length. The center bore is usually provided by drilling through the metal cell body. If the drilled opening is not sufficiently smooth a better surface may be obtained by the use of a reamer plus a polishing cloth or by any other suitable procedure. The center bore through the cell body provides another function in addition to reducing the void volume for sample flow. By keeping the diameter of the center bore the approximate diameter of the light transmitting window, the center bore acts as a light pipe to constrain the light emitted from a transmission probe. The directional constraint placed on the transmitted light effectively extends the dimension of the collimated light up to at least 20 centimeters. As a result, the transmission probe used to detect the transmitted light has a maximum efficiency for collecting the light energy transferred to the flow cell via the fiber optic cable between the light source and the flow cell.

Pipe weld connectors are preferred for use in the flow cell since they provide a cell which can operate at very high pressures up to 1,000 pounds per square inch or higher without leakage. It is within the scope of the invention, however, to use high pressure threaded connectors rather than pipe weld connectors.

The flow cells of the invention provide a substantial advantage over flow cells contained in cross unions in that the flow cells of the invention can operate successfully with optical path lengths several times greater than the optical path length obtainable in a union cross flow cell. Laboratory tests were carried out with a one quarter inch union cross flow cell similar to that described in Ser. No. 07/546,592. The optical path length of the one quarter inch union cross flow cell was extended from 2 centimeters to 8 centimeters by using standard one quarter inch tube fittings. The optical length extension was made by placing threaded tube extenders on opposite sides of the cross while at the same time maintaining the o-ring seal described in Ser. No. 07/546,592. Tests showed that it was possible to use a four centimeter optical path length without excessive loss of light intensity. Distances greater than 4 centimeters, however, caused a significant loss of the light intensity collected by a transmission probe positioned opposite the emitting transmission probe. The tests also showed that the extended union cross was prone to develop bubbles that became trapped within the optical path. The entrapped bubbles caused the transmitted light to be scattered which in turn interfered with the light transmission measured at the opposite end of the optical path. The tests also showed that the extended cross union had regions near both optical transmission probes that could be classified as "dead volume" zones. These dead volume zones were not readily flushed by the incoming flow and as a result, significantly reduced the speed with which a response could be measured for a composition change in the sample flowing through the cell.

Figure 4:
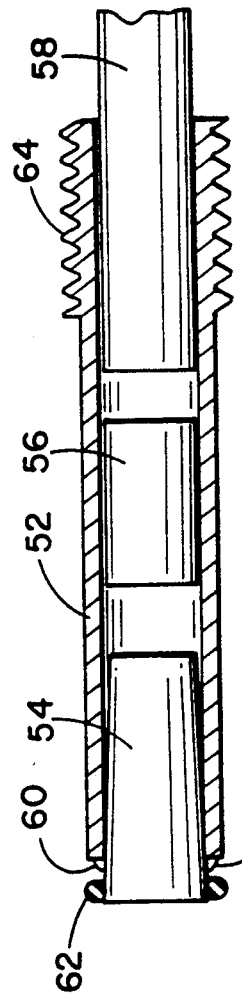
FIG. 4 is a more detailed schematic illustration of a fiber optic probe suitable for installation in the metal cell body of FIG. 3.

FIG. 4 shows a more detailed schematic in cross section of a fiber optic probe 50. In this figure, the transparent light transmitting window 54 is inserted in tube 52. Adjacent window 54 is a collimating lens 56 which may be made of silica or other suitable material. Adjacent the collimating lens is an optical fiber cable 58 through which light is transmitted to the collimating lens. Light leaving collimating lens 56 passes through window 54 and through the sample to be measured. The opening between tube 52 and light transmitting window 54 is sealed with a suitable sealing material 60. An o-ring gasket 62 is placed around light transmitting window 54. When the probe is inserted into connector 38 (FIG. 3), the o-ring is compressed between the end of tube 52 and the right angle shoulder described in the discussion of FIG. 3. Compression of o-ring 62 provides complete coverage of seal 60 thereby eliminating exposure of seal 60 to any corrosive material in the sample being measured. Probe 50 is affixed to connector 38 by a nut and ferrule assembly (not shown) of either the two-piece or one-piece type. Tube 52 is threaded at 64 to receive a fitting by which optical fiber 58 is affixed to tube 52.

The o-ring used in the flow cell of the invention serves two important functions. Primarily it protects the seal between the transparent light-transmitting window and the probe tube from the corrosive sample. It also prevents damage to the probe in the event that the seal is not totally effective and allows leakage of the corrosive sample into the probe. The o-ring may be made of a variety of materials depending on the particular chemical or chemicals contained in the samples being measured. In an atmosphere of hydrofluoric acid, fluoroelastomers such as Kalrez ® are used. Various chloroprene polymers may also be used in this service. For less corrosive atmospheres and for lower temperatures, other materials such as silicone rubber, neoprene, etc. may be used for the o-ring.

Effective coverage of seal 60 by o-ring 62 is obtained by hand pressure when the flow cell is assembled. However, if desired, a measured pressure on the o-ring may be provided by a suitable apparatus constructed to grip both the metal cell body and probe during assembly.

In samples containing hydrofluoric acid, the metal cell body is usually constructed of high nickel steel alloys such as Hastelloy C276. Monel may also be used with hydrogen fluoride and hydrogen chloride at lower temperatures. Depending on the type of corrosive atmosphere, stainless steels such as 316 stainless steel may also be used in the construction of the metal cell body.

The transparent light-transmitting window used in the fiber optic probes is usually made of sapphire, however, other materials such as diamond may also be used. Under milder corrosive conditions, other materials such as quartz may also be employed. The transparent light-transmitting material is sealed in the probe tube with a sealing material which provides an effective seal at the temperature of the sample being measured. Usually, fused glass is preferred, however, at lower temperatures, polymeric materials such as epoxies may be used.

In the construction of the probe, the transparent light-transmitting window usually extends out from the probe tubing for a distance of about one eighth inch to about one quarter inch. The minimum length of extension will be the width of the o-ring. The probes may be installed in the metal cell body at any distance up to 10 centimeters or as high as 20 centimeters apart. As stated previously, proper location of the right angle shoulders described in the discussion of FIG. 3 sets the optical path length of the probe. This eliminates time consuming measurements when the probe is removed from the metal cell body and then reassembled. Operations of the probe at more than one optical path length may be provided by the use of several metal cell bodies of different lengths in each of which the right angle shoulders are located to provide different optical path lengths by connectors 38.

The following examples are presented in illustration of the invention.

EXAMPLE 1

A flow cell as shown in FIG. 2 was constructed from a three quarter inch 316 stainless steel rod approximately four and one half inches long. The rod was drilled to receive one quarter inch probes and provide an optical path length of ten centimeters. Dummy probes were installed in the flow cell and tested at 1000 psi for one hour. No leaks were observed from the flow cell and there was no movement of the probes.

EXAMPLE 2

The flow cell of Example 1 was assembled with two fiber optic probes. The o-rings used in the probes were made of Kalrez fluoro-elastomer which is resistant to highly corrosive materials such as hydrogen fluoride, hydrogen chloride, chlorine caustics and the like. Optical performance tests for the assembled flow cell were carried out with a Guided Wave Inc. Model 200 analyzer (spectrometer). All of the tests showed that the two transmission probes were in optical alignment and that the flow cell transmitted sufficient light intensity to produce an acceptable signal/noise value for the quantitative spectrophotometric measurements.

Figure 5:
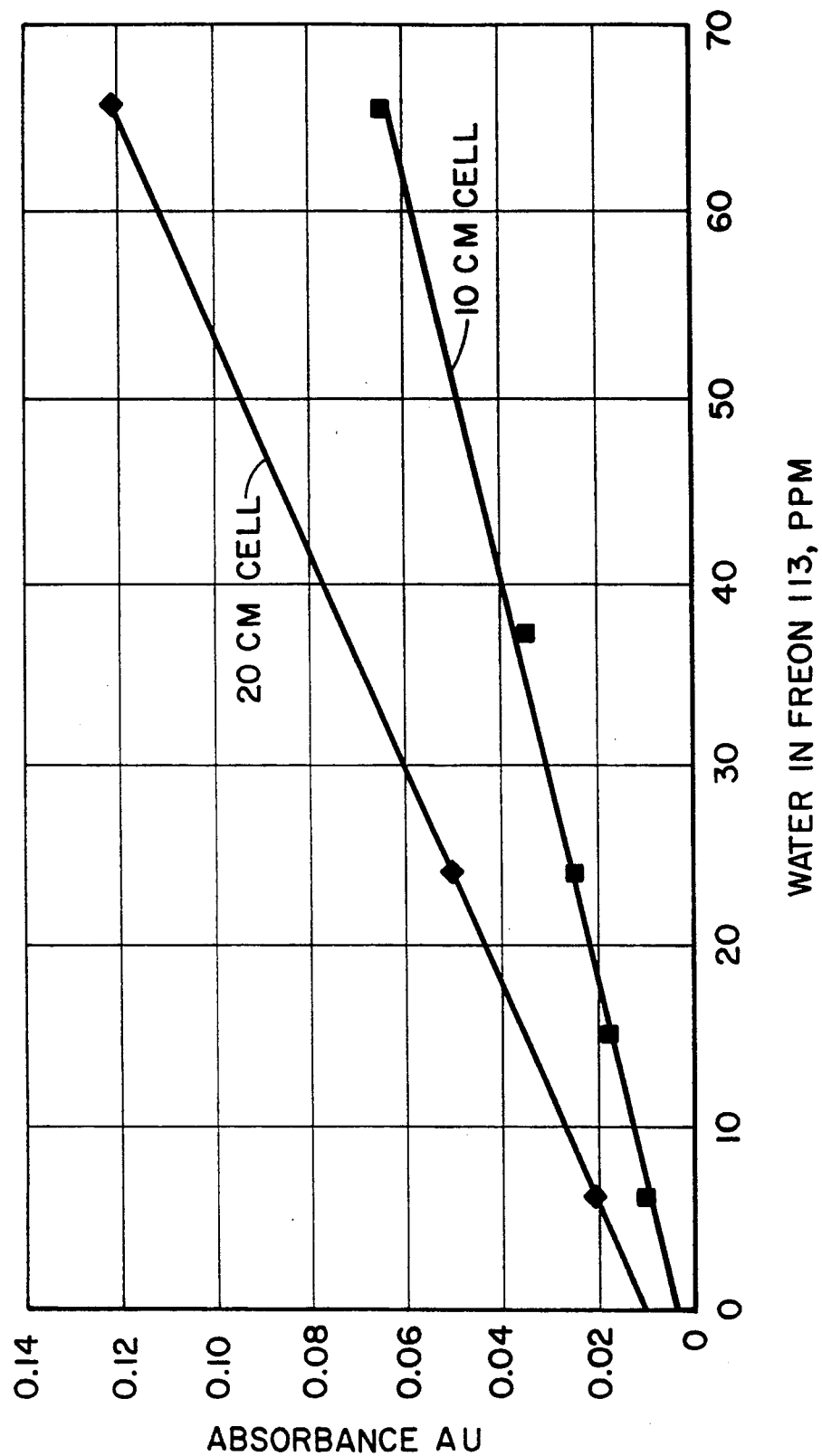
FIG. 5 is a plot showing the relationship between water concentration in Freon 113 and peak absorbance measured at 1886 nanometers in a flow cell having an optical path length of 10 cm and one having an optical path length of 20 cm.

The assembled flow cell was tested for analytical performance using Freon 113 containing trace quantities of water. All tests were conducted at atmospheric pressure and ambient temperature. FIG. 5 shows an example of an analytic calibration made with this (10 cm path length) flow cell. The results from the tests showed that the dissolved water content of the Freon 113 could be determined within plus or minus five parts per million for the concentration range of 0 to 65 parts per million. During the calibration tests, it was determined that the optical path length was void of bubble formation and that the sample flow into the cell was free of any significant dead volume.

EXAMPLE 3

A pilot plant test using the assembled flow cell of Example 2 was carried out over a five month period. The operating conditions for the test were ambient temperature and 50 psig pressure. The system was exposed to continuous flow of a chloro-fluorocarbon recycle stream. During the test, there was no evidence that any bubbles lodged in the optical path of the cell. Inspection of the disassembled cell at the conclusion of the test showed that the cell assembly and the transmission probe surfaces were in good condition. There was no evidence of corrosion of the flow cell and no indication of abrasive or etching deterioration of the glass seal surrounding the sapphire window.

EXAMPLE 4

The flow cell of Example 3 was installed in a laboratory circulation loop. A pump was used to circulate 2.0 molar potassium hydroxide solution (11 weight percent) from a 500 milliliter reservoir through the cell and back to the reservoir. The temperature of the system was ambient, which was 20° C. The solution was circulated for about one month. Disassembly of the flow cell indicated no noticeable deterioration in the flow cell or the o-ring assembly. The sapphire window was in the same condition as at the start of the test.

EXAMPLE 5

A flow cell was constructed from 3/16 stainless steel using the same design as the flow cell of Example 1 except that the optical path length was 20 centimeters rather than 10 centimeters. Tests made with the assembled 20 centimeter flow cell showed that there was sufficient transfer of radiant energy from the fiber optic emitting probe to the fiber optic collecting probe to make quantitative absorbance measurements. FIG. 5 shows a comparison of analytical calibrations made with Freon 113 containing traces of water using both the 10 centimeter flow cell of Example 2 and the 20 centimeter flow cell. This figure clearly shows that substantially greater absorbance is obtained with the 20 centimeter cell as compared to the 10 centimeter cell. This means that substantially lower concentrations of a material in a sample may be measured with the 20 centimeter cell as compared to the 10 centimeter cell.

The foregoing examples illustrate that it is possible through the use of the fiber optic flow cell of the invention to monitor process streams when highly corrosive materials are present without deterioration of the sealing material between the light-transmitting, transparent window and the tube holding such window. The examples further illustrate that substantially smaller quantities of materials in sample streams may be determined through the substantial increase in optical path length provided by the fiber optic cells of the invention.

The fiber optic cells have been shown as being manufactured from a cylindrical metal cell body, however, this is only for convenience and the availability of this type of metal stock. It is, of course, within the scope of the invention to use metal stock which is square in shape or which has any other desired shape. The inlet and outlet openings in the flow cell for ingress and egress of samples have been shown in alignment. However, again, this is only for convenience in manufacturing the flow cell. Such openings may be positioned in any manner in relationship to each other as long as they are placed at appropriate end positions in the flow cell.

While certain embodiments and details have been shown for the purpose of illustrating the present invention, it will be apparent to those skilled in that art that various changes and modifications may be made herein without departing from the spirit or scope of the invention.

We claim:
1. A flow cell suitable for use in a corrosive environment which comprises:
   (a) an extended metal cell body containing a smooth longitudinal circular center bore of uniform cross-section,
   (b) a circular opening at each end of the cell body extending perpendicularly into the center bore, adapted to receive a sample entry line at one end of the center bore and sample discharge line from the other end of the center bore,
   (c) a circular connector in each of the opposing ends of the cell body communicating axially with the center bore and abutting the cell body, said circular connector having an inside diameter greater than the inside diameter of the center bore, whereby a right angle shoulder is formed between the inside of the circular connector and the abutting cell body surrounding the center bore,
   (d) a fiber optic probe positioned in each circular connector, each probe having a light-transmitting, transparent window extending from a tube contained in each probe, said tube abutting said right angle shoulder,

(e) an opening between each tube and light-transmitting window, said opening being sealed with a sealing material which is attacked by the corrosive environment, and (f) a corrosive resistant o-ring gasket positioned compressively between the end of each tube and said right angle shoulder, thereby protecting the sealing material from the corrosive environment.

2. The flow cell of claim 1 in which a circular connector of larger cross-section than said circular opening extending perpendicularly into the center bore is provided in each end of the cell body in axial alignment with each said circular opening.

3. The flow cell of claim 2 in which all of the circular connectors in the cell body are welded to the cell body and are threaded at the outer ends to provide attachment of the fiber optic probes and sample entry and discharge lines.

4. The flow cell of claim 3 in which the circular opening at each end of the cell body extending perpendicularly into the center bore has substantially the same cross-section as the center bore.

5. The flow cell of claim 1 in which the light-transmitting, transparent window is sapphire.

6. The flow cell of claim 5 in which the sealing material is glass.

7. The flow cell of claim 6 in which the sealing material is melted glass coated with epoxy plastic.

8. The flow cell of claim 7 in which the corrosive-resistant, o-ring seal is constructed from a material selected from the group consisting of a fluoro-elastomer, a chloroprene polymer, silicone rubber and neoprene and mixtures thereof.

9. The flow cell of claim 8 including means for receiving or sending a signal to or from a spectrometer and a computer.

10. A flow cell suitable for use in a corrosive environment which comprises:
 (a) an extended metal cell body containing a smooth longitudinal circular center bore of uniform cross-section,
 (b) a circular opening at each end of the cell body extending perpendicularly into the center bore, adapted to receive a sample entry line at one end of the center bore and sample discharge line from the other end of the center bore,
 (c) a circular connector in each of the opposing ends of the cell body communicating axially with the center bore and abutting the cell body, said circular connector having an inside diameter greater than the inside diameter of the center bore, whereby a right angle shoulder is formed between the inside of the circular connector and the abutting cell body surrounding the center bore,
 (d) a fiber optic probe positioned in each circular connector, each probe having a light-transmitting, transparent window extending from a tube contained in each probe, said tube abutting said right angle shoulder and said window extending into the center bore a sufficient distance so that the face of said window is in vertical alignment with the nearest internal surface of the circular opening into the center bore,
 (e) an opening between each tube and light-transmitting window, said opening being sealed with a sealing material which is attacked by the corrosive environment, and
 (f) a corrosive resistant o-ring gasket positioned compressively between the end of each tube and said right angle shoulder, thereby protecting the sealing material from the corrosive environment.

11. The flow cell of claim 10 in which a circular connector of larger cross-section than said circular opening extending perpendicularly into the center bore is provided in each end of the cell body in axial alignment with each said circular opening.

12. The flow cell of claim 11 in which all of the circular connectors in the cell body are welded to the cell body and are threaded at the outer ends to provide attachment of the fiber optic probes and sample entry and discharge lines.

13. The flow cell of claim 12 in which the circular opening at each end of the cell body extending perpendicularly into the center bore has substantially the same cross-section as the center bore.

14. The flow cell of claim 10 in which the light-transmitting, transparent window is sapphire.

15. The flow cell of claim 14 in which the sealing material is melted glass.

16. The flow cell of claim 15 in which the sealing material is melted glass coated with epoxy plastic.

17. The flow cell of claim 16 in which the corrosive-resistant, o-ring seal is constructed from a material selected from the group consisting of a fluoro-elastomer, a chloroprene polymer, silicone rubber and neoprene and mixtures thereof.

18. The flow cell of claim 17 including means for receiving or sending a signal to or from a spectrometer and a computer.

19. The flow cell of claim 11 in which the light-transmitting window is sapphire.

20. The flow cell of claim 19 in which the melted glass is coated with an epoxy plastic.

21. The flow cell of claim 20 in which the o-ring seal is constructed from a material selected from the group consisting of a fluoro-elastomer, a chloroprene polymer, silicone rubber and neoprene and mixtures thereof.

22. The flow cell of claim 11 including means for receiving or sending a signal from the fiber optic probes to or from a spectrometer and a computer.

23. The flow cell of claim 13 in which the light-transmitting, transparent window is sapphire.

24. The flow cell of claim 12 in which the light-transmitting, transparent window is sapphire.

25. The flow cell of claim 24 in which the sealing material is melted glass.

26. The flow cell of claim 25 in which the sealing material is melted glass coated with epoxy plastic.

27. The flow cell of claim 26 in which the corrosive-resistant o-ring seal is constructed from a material selected from the group consisting of a fluoro-elastomer, a chloroprene polymer, silicone rubber and neoprene and mixtures thereof.

28. The flow cell of claim 27 including means for connecting said flow cell to a spectrometer and a computer.

* * * * *